(12) United States Patent
Sage et al.

(10) Patent No.: US 6,932,796 B2
(45) Date of Patent: Aug. 23, 2005

(54) LIQUID METERING SYSTEM

(75) Inventors: Burton H. Sage, Vista, CA (US); Brian E. Catanzaro, San Diego, CA (US)

(73) Assignee: Tearafuse, Inc., Carlsbad, CA (US)

( * ) Notice: Subject to any disclaimer, the term of this patent is extended or adjusted under 35 U.S.C. 154(b) by 0 days.

(21) Appl. No.: 10/146,588

(22) Filed: May 15, 2002

(65) Prior Publication Data

US 2003/0213297 A1 Nov. 20, 2003

(51) Int. Cl.[7] .............................. A61M 5/00; A61B 6/00; G01J 5/02; G01F 1/708; G01N 15/06
(52) U.S. Cl. .................. 604/250; 600/477; 250/339.06; 250/341.6; 250/574; 73/861.95; 356/28
(58) Field of Search ............................. 604/30, 31, 33, 604/34, 65, 67, 93.01, 113, 250, 251, 253, 257; 600/407, 473, 475, 476, 477; 250/338.1, 338.3, 338.5, 339.1, 339.04, 339.06, 340, 341.1, 341.2, 341.3, 341.6, 341.8, 573, 574, 575, 339.6, 339.4; 73/861.95; 356/28, 28.5; 137/468

(56) References Cited

U.S. PATENT DOCUMENTS

| | | | |
|---|---|---|---|
| 3,469,578 A | 9/1969 | Bierman | |
| 4,318,400 A | 3/1982 | Peery et al. | |
| 4,340,083 A | 7/1982 | Cummins | |
| 4,447,224 A | 5/1984 | DeCant, Jr. et al. | |
| 4,447,232 A | 5/1984 | Sealfon et al. | |
| 4,468,221 A | 8/1984 | Mayfield | |
| 4,532,811 A | * 8/1985 | Miller, Jr. et al. | 73/861.95 |
| 4,600,302 A | * 7/1986 | Sage, Jr. | 356/39 |
| 4,741,736 A | 5/1988 | Brown | |
| 4,777,368 A | * 10/1988 | Kerlin, Jr. | 250/341.6 |
| 4,874,386 A | * 10/1989 | O'Boyle | 604/246 |
| 4,886,499 A | 12/1989 | Cirelli et al. | |
| 4,938,079 A | * 7/1990 | Goldberg | 73/861.95 |
| 4,938,368 A | 7/1990 | Sharman | |
| 5,016,047 A | 5/1991 | Meacham | |
| 5,061,242 A | 10/1991 | Sampson | |
| 5,163,920 A | 11/1992 | Olive | |
| 5,211,626 A | * 5/1993 | Frank et al. | 604/65 |
| 5,248,300 A | 9/1993 | Bryant et al. | |
| 5,527,288 A | 6/1996 | Gross et al. | |
| 5,533,412 A | * 7/1996 | Jerman et al. | 73/861.95 |
| 5,575,770 A | 11/1996 | Melsky et al. | |
| 5,665,070 A | 9/1997 | McPhee | |
| 5,741,979 A | * 4/1998 | Arndt et al. | 73/861.05 |
| 5,848,990 A | 12/1998 | Cirelli et al. | |
| 5,984,894 A | 11/1999 | Poulsen et al. | |
| 6,074,369 A | 6/2000 | Sage et al. | |
| 6,162,202 A | 12/2000 | Sicurelli et al. | |
| 6,386,050 B1 | * 5/2002 | Yin et al. | 73/861.95 |
| 6,582,393 B2 | * 6/2003 | Sage, Jr. | 604/65 |

FOREIGN PATENT DOCUMENTS

EP    1 177 802    6/2002

* cited by examiner

Primary Examiner—Nicholas D. Lucchesi
Assistant Examiner—Mark K. Han
(74) Attorney, Agent, or Firm—Foley & Lardner; Martin Cosenza

(57) ABSTRACT

Systems and methods for measuring the flow of a liquid along a conduit are disclosed. A heat source applies thermal energy to a portion of a liquid flowing along a conduit thereby elevating its temperature. An optical sensing means comprising a light source illuminating the liquid in the conduit downstream from the position of application of the thermal energy and an optical detector receiving a portion of this illumination senses the heated portion of liquid by measures a change in an optical property of the illumination caused by a change in the index of refraction of the heated portion of liquid. The time required for the heated portion of the liquid to move from the point of application of thermal energy to the point of optical sensing is measured. This measured time, along with the distance of separation of the heat source and the optical sensing means permits calculation of the velocity of the liquid in the conduit.

27 Claims, 4 Drawing Sheets

LIQUID METERING SYSTEM

This application claims subject matter disclosed in copending application Ser. No. 09/867,003 filed May 29, 2001.

BACKGROUND OF THE INVENTION

A. Field of the Invention

This invention relates to the measurement of properties of liquids moving in a conduit and specifically the measurement of the flow rate of a liquid moving at a relatively low flow rate of less than one liter per minute in a conduit. Most specifically, it relates to the measurement of the rate of infusion of therapeutic agents to patients to achieve highly accurate dosing of these patients according to a prescribed administration regimen.

B. Related Art

Many methods of measuring the flow rate of liquids, and in particular the rate of infusion of a pharmaceutical to a patient are known. Best known are positive displacement systems wherein a known volume of fluid is moved over time independent of other system parameters such as pressure and liquid viscosity. Today, the most commonly used positive displacement pump for accurate infusion of a pharmaceutical to a patient is the syringe pump. A motor moves a plunger down the barrel of a syringe with tightly controlled manufacturing tolerances on inside diameter. The rate of advance of the plunger times the time of advance times the cross-sectional area of the syringe determines the volume of fluid infused. This positive displacement method is used, for example, in the MiniMed Model 508 insulin pump, the current market share leader in insulin pumps. The suggested retail price for the MiniMed 508 pump is $5,995.00. A second example of a positive displacement system is the peristaltic pump, where rollers placed against a flexible conduit roll along the conduit to move the fluid down the conduit. In peristaltic pumps, enough force is applied to the liquid in the flexible conduit to eliminate any dependence on pressure and viscosity. However, the volume of liquid dispensed remains dependent on the volume of fluid in the tubing, which depends on the square of the inside diameter of the elastomeric tubing. Since the manufacturing tolerance on the inside diameter of economic elastomeric tubing is on the order of +/-10%, the delivery accuracy is limited to +/-20%. Peristaltic pumps are also expensive, but somewhat less expensive that syringe pumps. Today, peristaltic pumps are seldom used for accurate delivery of pharmaceuticals.

Given the expense of these positive displacement pumps, and the need to find less expensive systems for accurate delivery of pharmaceuticals, many other devices and methods have been proposed to maintain the required level of accuracy while reducing the cost. It is clear that many of these proposed systems achieve the goal of reduced expense. However, the problem that these proposed schemes face is that they do not achieve the required accuracy of delivery of the pharmaceutical. For example, in a liquid dispensing system with a pressurized liquid container where the pressure on the liquid forces it along the conduit, the parameters dictating the flow include the pressure that is causing the liquid to flow, the inside diameter of the conduit along which the liquid is flowing, the length of the conduit, and the viscosity of the liquid, which is in turn dependent on the temperature of the liquid. This problem is further compounded by the fact that the dependence on the inside diameter of the conduit is a fourth power dependence. In many delivery systems of this type, the pressure on the liquid decreases as the amount of liquid in the container decreases, leading to a reduction in the flow rate. The solution to this pressure decrease is known. O'Boyle in U.S. Pat. No. 4,874,386, teaches a liquid dispensing device that accurately controls the pressure in this type of dispensing system by incorporating a constant pressure spring. But the dimensions of the flow conduit, its cross section, and the temperature for viscosity control are left uncontrolled, with the result of inaccurate dispensing of the fluid.

In order to overcome the situation of having to manufacture dispensing system components to higher tolerances than is economically feasible, many methods of measuring the liquid flow rate have been taught. If the actual flow rate is measurable, the flow rate may be adjusted to the desired flow rate. Or, if an accurate total volume rather than flow rate is required, the required time of flow may be calculated using the actual flow rate to achieve the desired volume.

In general, the different types of liquid flow measuring systems can be divided into two classes—those that require contact with the liquid to measure the flow, and those that measure the flow without requiring contact with the liquid. Flow measuring systems in the first class include a) turbines, where the angular speed of the propeller in the stream is a measure of flow rate, b) pressure drop systems, where the pressure difference across a flow resistor is used to calculate the flow rate, and c) certain forms of "thermal time of flight" systems where elements that add heat to the stream and measure heat in the stream are used to measure flow rate. Examples of these "thermal time of flight" systems are taught by Miller, Jr. in U.S. Pat. No. 4,532,811 and by Jerman in U.S. Pat. No. 5,533,412. However, in many liquid delivery systems, the conduit along which the liquid flows requires frequent replacement and, in the case of pharmaceutical infusion systems, the total flow path must also be kept sterile. In this first class of types of flow meters, the added complexity of adding components, and their necessary leads and connectors to the replaceable conduits, causes the replacement conduits to be expensive. And if these additional components are added to a reusable portion of the dispensing system, the replacement of the liquid container, or addition of fresh liquid to an existing container opens the flow path to an unsterile environment. For these reasons, attention has been paid to the invention of the second class of flow meters—those that do not require contact with the liquid in the conduit and add complexity to the conduit.

Kerlin, Jr, in U.S. Pat. No. 4,777,368, teaches a method and apparatus for non-contact measurement of the velocity of a moving mass. In a preferred embodiment, an infrared heat source raises the temperature of an element of the moving mass and an infrared detector, viewing this element of the moving mass at a later time, detects the heated element and records the time required for the moving mass to move from heater to detector. Given the physical separation of the heater and the detector, the speed of the moving mass may be calculated. Kerlin makes reference to the use of this concept for liquids as well as solids. Goldberg, in U.S. Pat. No. 4,938,079 teaches the same basic concept as Kerlin, Jr. with the modification that microwave energy is used to heat the liquid within a conduit and a microwave detector is used to sense the heated liquid downstream from the heater. Frank et al in U.S. Pat. No. 5,211,626 also teaches a thermal time of flight flow metering method, and while at least one infrared detector is used to detect the heated liquid, the liquid is heated by thermal contact with the liquid through the wall of the conduit. Taught by Goldberg and Frank is the need for accurate delivery of the liquid (although Frank admits that his teachings apply only to relatively non-accurate delivery of the liquid) the need for a closed flow path, and the need for an inexpensive replaceable conduit. However, each of these patents fails to recognize that the measured time of flight and the calculated stream velocity are insufficient to completely correct for variations in system components. Flow rate, as measured in volume per unit time, requires not only a measurement of the time, but also the volume of liquid dispensed in that time. Or, if the measurement of velocity is made, as described in all three of these teachings, then to obtain the flow rate, the cross-sectional area of the conduit must be known. These above three teachings teach the measurement of time only. The volume component is critically dependent on the inside diameter of the conduit. If time is the measured parameter, then flow rate depends on the cross-sectional area of the column of liquid and the length of the column of liquid. The cross-sectional area depends on the square of the inside diameter of the conduit. As described above, typical tolerances on the inside diameter of a conduit, especially for conduits of relatively small inside diameter, are +/−10%. Hence the variation in volumetric flow rate, even given a perfectly accurate measurement of the time of flight, is +/−20%. And if the liquid velocity is calculated from the time of flight, the flow rate depends on the cross-sectional area, which, as described above, leads to a flow rate uncertainty of +/−20%. And in situations where the conduit is to be replaced frequently, unless the inside diameter of the conduit is measured by the device or measured in the factory and communicated to the device, both expensive steps, the uncertainty due to the unknown inside diameter remains. A device and method that achieves accurate measurement of flow rate, and hence accurate liquid delivery by compensating for both variations in the inside diameter of the conduit and the velocity of the liquid flowing in the conduit is disclosed in pending U.S. application Ser. No. 09/867,003 filed May 29, 2001. This application is incorporated herein by reference.

In the teachings of U.S. Pat. Nos. 4,777,368, 4,938,079, and 5,211,626 there are additional practical considerations that make these teachings difficult to reduce to practice in cost-effective commercial products. The first of these practical aspects is the heating of the portion of the liquid to be sensed. Due to the high heat capacity and the rapid thermal diffusivity of virtually all liquids of commercial importance, and especially water, which is the base of all pharmaceutical infusion fluids, heating the liquid fast enough and to a high enough temperature to realize an operation flow meter is very difficult. Kerlin, Jr. in U.S. Pat. No. 4,777,368 implicitly recognizes this by advocating a high power CO2 laser. Neither Frank in U.S. Pat. No. 5,211,626 nor Goldberg, in U.S. Pat. No. 4,938,368 recognize this problem. And the problem is especially acute for Frank since his teachings require the heat to pass through the wall of the conduit by conduction, which is especially time-consuming and lossy. A solution to this problem, which is not alluded to in any of these three teachings, is to stop the flow of the liquid and to heat the liquid while it is stationary. The flow rate is measured by restarting flow once the liquid is heated. The two advantages of stopping the flow to heat the liquid is that the total mass of liquid that must be heated is greatly reduced and the heat pulse is relatively confined in position along the conduit. This solution is taught in pending U.S. application Ser. No. 09/867,003.

The second practical aspect which makes the prior art teaching, including the teaching in pending U.S. application Ser. No. 09/867,003, difficult to commercialize is the mode of detecting the heat pulse. Many pharmaceutical solutions, especially protein solutions such as insulin, degrade at temperatures above room temperature, and begin to denature at temperatures above 40 deg centigrade. A preferred temperature rise would be less than 5 centigrade degrees above ambient. For these systems to operate successfully the heated portion of liquid must be accurately detected and its location along the conduit accurately measured. Detection methods relying on detecting the infrared radiation from such a small change in temperature, such as proposed by Frank in U.S. Pat. No. 5,211,626, Kerlin, Jr. in U.S. Pat. No. 4,938,079, and Sage, Jr. in pending U.S. application Ser. No. 09/867,003, must operate in the far infrared where detectors are either too slow to respond to the heated liquid or must be cooled, making them large, energy consuming and expensive. Goldberg in U.S. Pat. No. 4,938,079 is sensitive to this issue, but offers no data to support a practical or operational device.

Thus there continues to be a need for improved devices and methods for accurate and economical measurement of liquid flow in liquid dispensing systems, especially in the area of infusion of pharmaceutical solutions. This invention meets these needs.

An object of the current invention is to provide an accurate, inexpensive, and practical system and method for measuring the volumetric flow of a liquid in a conduit.

It is a further object of the current invention to use this system and method for measuring the volumetric flow of a liquid in a conduit to infuse pharmaceutical solutions. This flow rate may be used for either accurate delivery of the pharmaceutical solutions or, when zero flow rate is measured, to detect occlusions in a delivery system for pharmaceutical solutions.

It is yet another object of the current invention to provide an accurate, inexpensive and practical system and method for detecting and measuring the temperature of a liquid in a conduit.

SUMMARY OF THE INVENTION

The present invention provides for a device and method for measuring the time of flight and/or the velocity of a liquid moving in a conduit. The apparatus includes an optically transmissive conduit through which the liquid flows. A light source illuminates a portion of the liquid through the optically transmissive conduit. A portion of the illumination proceeds by reflection at the liquid conduit interface to a detector in one embodiment. A portion of the illumination proceeds by transmission through the conduit and liquid to a detector in a second embodiment. In a second embodiment, the light source is a coherent light source, and a second reference pathway is provided to the detector.

When a heated portion of the liquid, which has been heated upstream of the position of illumination of the liquid, flows through the illumination a property of the reflected or transmitted illumination changes due to the change of the index of refraction of the heated portion of the liquid. In the reflected illumination embodiment, the intensity of the reflected illumination changes. The detector detects this change. In the transmitted illumination embodiment, the phase of the transmitted illumination changes. The detector detects this change. The time required for the heated portion of the liquid to flow from the heating position to the detecting position is a measure of the time of flight of the liquid. When combined with the physical distance between the location of heating and the location of detection, this time of flight provides the velocity of the liquid. When combined with the cross sectional area of the conduit, provided the conduit is of uniform inside diameter, this liquid velocity provides the volumetric flow rate of the liquid.

Other aspects and advantages of the invention will become apparent from the following detailed description and drawings of two embodiments of the invention.

DETAILED DESCRIPTION OF THE INVENTION

Figure 1:
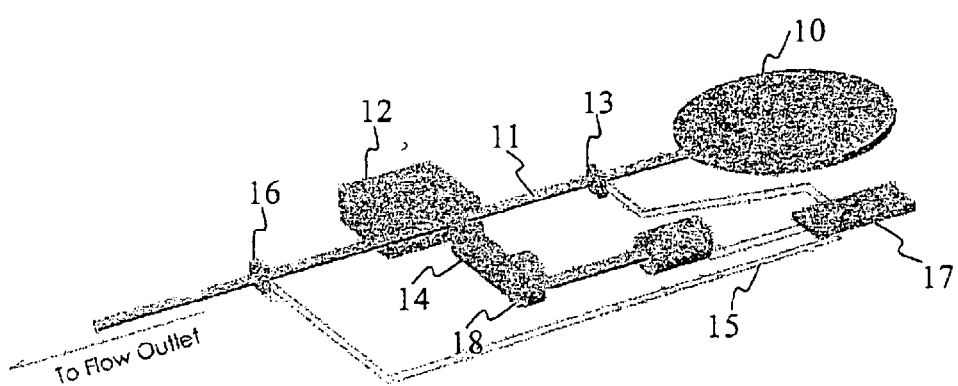
FIG. 1 is a function block diagram of a liquid dispensing system with a flow meter designed according to the invention.

The optical flow meter of this invention will be described in terms of a liquid dispensing system for use in infusion of pharmaceutical solutions. FIG. 1 shows a block diagram of such a system. The liquid to be dispensed is contained in pressurized reservoir 10. When pinch tube member 14 is moved away from stop 12, conduit 11 is opened and the liquid is free to flow down conduit 11 to the flow outlet. When pinch tube 14 presses conduit 11 against stop 12, stopping flow, the liquid is not free to move down the conduit to the flow outlet. At a selected time, microprocessor 17 signals heating element 13 to heat the portion of the liquid at its location along the conduit. Once the portion of the liquid is heated, the pinch tube member is moved away from the conduit, and the liquid begins to flow. At some later time, the heated portion of the liquid passes heat sensor 16 where the heated portion is detected. The time required for the heated portion of the liquid to move from the location of the heater to the heat sensor is measured. Additionally, the velocity of the liquid may be calculated by dividing the distance between the heating element 13 and the heat sensor 16 by the measured elapsed time.

Figure 2:
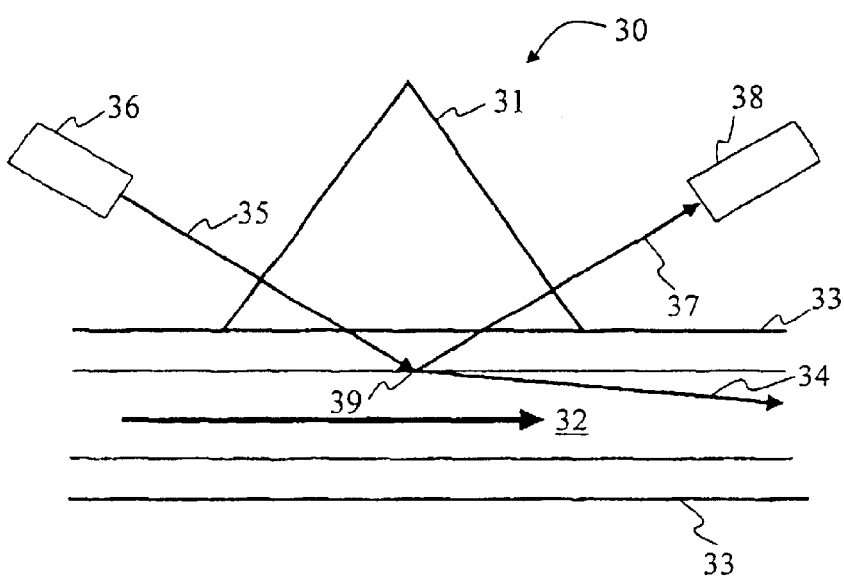
FIG. 2 is an optical schematic of the portion of the liquid flow meter where the change in the index of refraction is detected by measuring the change in the intensity of light reflected from the inside surface of the conduit.
Figure 4:
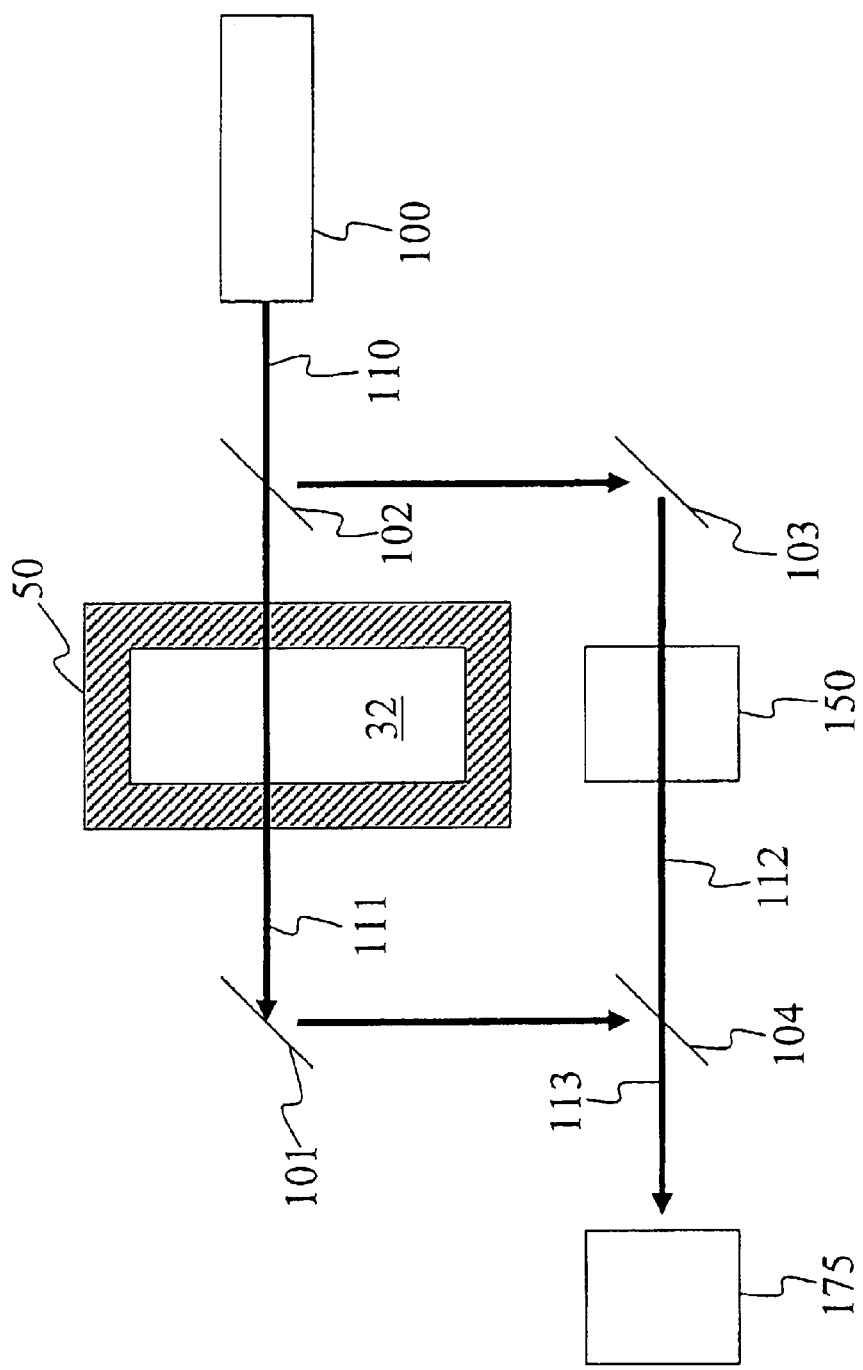
FIG. 4 is an optical schematic of the portion of the liquid flow meter where the change in the index of refraction of the liquid is detected by measuring the difference in phase difference between coherent light transmitted through the conduit and a reference light path.

A first preferred embodiment of heat sensor 16 is shown in FIG. 2. Within heat sensor 16 is optical detector 30. Conduit 11 of FIG. 1 is shown in section with conduit wall 33 and conduit lumen 32. Conduit wall 33 is optically transparent, made of any material capable of achieving optically smooth surfaces but preferably made of glass. Also preferably, conduit wall 33 has at least one flat side. One trivial example of conduit 11 is square or rectangular in cross section, as shown in FIG. 4. Prism 31 is in optical contact with conduit wall 33. Prism 31 is preferably mounted on conduit wall 33 by optical cement but may be mounted on conduit wall 33 with an optical index matching medium or conduit 11 and prism 31 may be an integral structure. Optical prism 31 is also made of any optically transparent material capable of achieving optically smooth surfaces such as glass or polycarbonate. Preferable, the index of refraction of conduit 11 and prism 31 are matched at the wavelength of light from light source 36.

Figure 3:
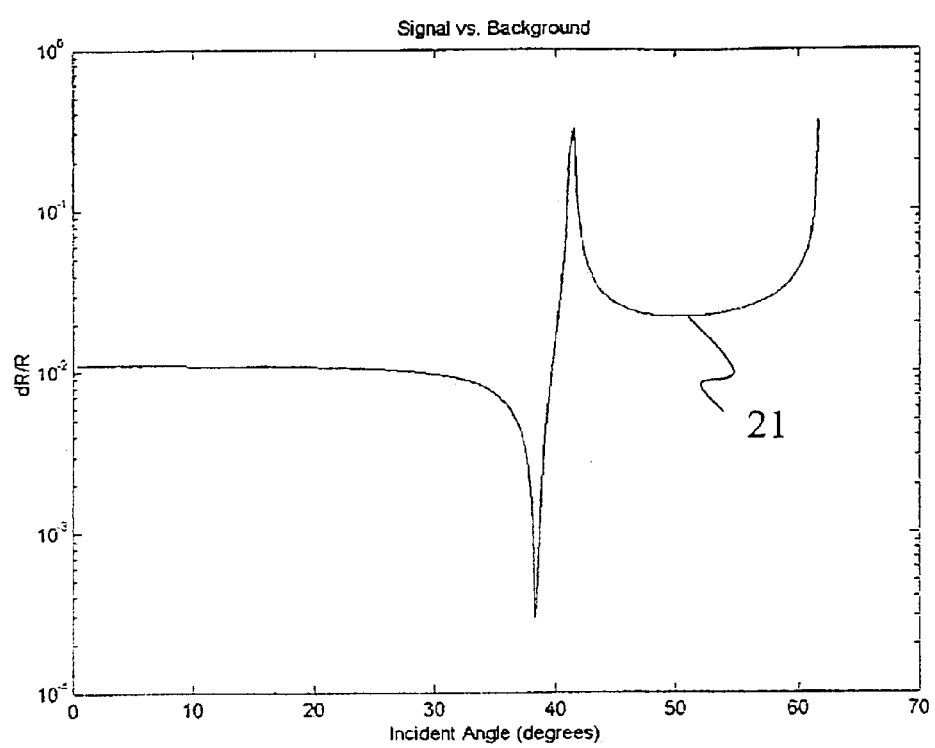
FIG. 3 is a theoretical plot of the intensity of the light reflected from the inside surface of a glass conduit when water is flowing as a function of the angle of incidence of the light from a light source.

Light from light source 36 follows path 35 and is preferably normally incident on the left surface of prism 31. Light from light source 36 continues through the interface between prism 31 and the outside surface of conduit 11, through conduit wall 33 to the interface between the inside wall of conduit 11 and the liquid in lumen 32 at point 39. At this interface at point 39, light is both reflected (beam 37) and refracted (beam 34). The reflected light beam 37 proceeds out of prism 31, preferably normal to the right surface of prism 31 and proceeds to light detector 38. The fraction of the intensity of light 35 that is reflected at point 39 to form light beam 37 may be calculated using the standard Fresnel equations. A graph of this calculation for all angles of incidence from normal incidence (where beam 35 would be normal to conduit outside surface 33) to the critical angle (where total internal reflection occurs) is shown in FIG. 3. The materials used for this calculation are BK-7 glass for prism 31 and conduit 11 and water for liquid 32. Shown in this figure is the reflected energy for P polarization. The preferred embodiment utilizes P polarization for beam 35 because of the larger reflected signal. The light detector will typically be monitoring changes in reflectance, not absolute reflectance. As a consequence, it is more germane to calculate the change in the reflected light (beam 37) as a function of angle for a given change in temperature of the fluid. Solid curve 21 in FIG. 3 shows the percentage change in the reflected light (beam 37) as a function of reflected angle for a change in fluid temperature of 10 centigrade degrees. As can be seen from the solid curve 21 in FIG. 3, there is a range of angles of incidence from about 45 degrees to nearly 60 degrees where the percent change in the reflected signal is relatively large (about one percent of the reflected intensity) and relatively independent of the angle of incidence. The intensity of the refracted light in light beam 34 is the difference between the incident intensity and the reflected intensity. This light is directed down the flow tube, away from light sensor 38.

When light source 36 of FIG. 2 emits steady illumination, and the temperature of liquid 32 remains constant, the intensity of light beam 37 is constant, and detector 38 detects no change in the intensity of light beam 37. However, when the portion of liquid in lumen 32 that has been heated by heat source 13 in FIG. 1 passes point 39, the intensity of light beam 37 will change as a consequence of the dependence of the index of refraction of fluid 32 on temperature. For example, in the preferred embodiment, heated water has a lower index of refraction than cooler water, thus more light will reflect when water of a higher temperature is present at location 39. In one specific embodiment, the incident/reflected angle is 60 degrees, the water temperature is 20 centigrade degrees prior to heating and 25 centigrade degrees after heating. In this specific embodiment, 10% of the incident light is reflected for water prior to heating as shown by the dashed curve in FIG. 3. Once heated water is present at location 39, the signal will increase by 1%. Thus, one milliwatt illumination will present a constant signal of 100 microwatts to detector 38 via beam 37. When heated water (25 centigrade degrees) is present at location 39, the signal will increase to 101 microwatts. Given today's laser and detector components, generating and detecting these signals are routine.

Note that with the appropriate conduit 11, it is possible to detect the presence of the heat pulse in liquid in lumen 32 by detecting a change in intensity in refracted light beam 34. While this is a much larger base signal (approximately 90% of the intensity incident at point 39 is in light beam 34), the magnitude of the change in the intensity of light beam 34 due to the passing heat pulse in liquid 32 is equal to that received by detector 38 shown in FIG. 2.

The output from detector 38 in FIG. 2 is an electronic signal that changes with the temperature of the heat pulse in liquid 32. This electronic signal may be subjected to either analog or digital processing to measure the time of flight from the location of heat source 13. By analog processing, the signal may be differentiated, and the axis crossing of the differentiated signal would be a measure of the location in time of the peak of the heat pulse in liquid 32. The time of this axis crossing could be used to identify the time when the peak of the heat pulse passed location 39 in FIG. 2. This and alternate methods of processing an analog electronic signal to locate the heat pulse in time are known to those skilled in the art of analog signal processing. Alternately, the electronic signal from detector 38 could be processed digitally to locate the heat pulse in time. The center of gravity of this electronic signal could be calculated, and the location in time of this center of gravity could be used to measure the time required for the heat pulse to move from the heat source 13 to location 39 in FIG. 2.

A second preferred embodiment for heat sensor 16 in FIG. 1 is an interferometric measurement of the index change induced by temperature in liquid 32. A specific embodiment of this concept with a Michelson interferometer is shown schematically in FIG. 4. However, with the appropriate illumination, detection, and construction, other interferometer configurations are applicable.

Shown in FIG. 4 is a specific embodiment of conduit 11: a rectangular conduit 50 containing liquid in lumen 32. Conduit 50 is optically transparent and manufactured from any material capable of achieving optically smooth surfaces on both the inside and outside surfaces of the top and bottom of conduit 50. Optical glass is preferred, but certain optical polymers such as polycarbonate would also be acceptable.

Also shown in FIG. 4 is coherent light source 100. Light source 100 is preferably a laser, but any light source with the appropriate coherence length would be appropriate. Elements 102 and 104 are beamsplitting elements, preferably 50% transmissive and 50% reflective. Elements 101 and 103 are reflective mirrors. Element 175 is a detector suitable for detecting the emission of light source 100. In one embodiment, element 150 is an optical path delay element (e.g. glass, polycarbonate, fiber loop, et. al.). In this embodiment, it is preferred that the delay element provides a precise delay of one half of the wavelength of illumination. In another embodiment, element 150 is a separate section of conduit 50 where the liquid in lumen 32 has not been heated.

Light beam 110 emanates from source 100. This beam is split into two paths by beamsplitter 102. One beam, 111 passes through conduit 50 and subsequently fluid the liquid in lumen 32. Depending on the definition of element 150, beam 112 may pass through air, an optical delay element, or a separate section of conduit 50. Beam 111 is reflected by mirror 101 and redirected towards beamsplitter 104. Beam 112 is reflected by mirror 103 and redirected towards beamsplitter 104. Beamsplitter 104 combines beams 111 and 112 into beam 113. Beam 113 is now the coherent sum of the two beams, 111 and 112. The phases of beams 111 and 112 add, creating an intensity pattern that is dependent upon the phase delay induced by the liquid in lumen 32. This intensity pattern is detected by detector 175.

When fluid 32 is heated, the index of refraction changes. As a consequence, so does the phase of beam 111. This in turn causes an intensity variation that is detected by detector 175. In the specific embodiment where element 150 produces an optical delay of precisely one half of a wavelength in beam 112 prior to heating the liquid in lumen 32, the intensity detected by detector 175 will be very small. Then, when fluid 32 is heated, the percentage change in intensity at detector 175 will be very large.

The electrical signal may be processed in ways similar to the electrical signal described earlier for the first embodiment where the heat pulse is detected as a change in illumination reflected from point 39 in FIG. 2.

The descriptions of these two embodiments illustrate how a heated segment of a liquid in a conduit may be used to measure the flow of the liquid down the conduit, thereby providing information allowing the calculation of the velocity of the liquid in the conduit. In pharmaceutical applications, such measurements provide the basis for the more accurate delivery of the pharmaceutical solution. Also in pharmaceutical delivery applications, especially during intravenous administration when the conduit is part of an IV administration set and the motion of the liquid is caused by gravity or an infusion pump, there is also a need to verify that the liquid path stays open. Frequently, for example when a patient rolls over, the administration set may be crimped, stopping flow even though the infusion pump is operating or there is adequate head on the gravity flow system. The flow sensor of this invention is also capable of the rapid detection of this situation. Whenever such an occlusion of the conduit occurs, the heated segment of the liquid does not move when the pinch tube is opened. Hence the detector does not detect any change in an optical property of the illumination. The absence of a detected signal from the heated segment of the liquid is then a measure of lack of flow, which may be caused by an occlusion in the conduit or a number of other possibilities. Thus the flow sensor of this invention also provides for the detection of flow system failures, among which is an occluded conduit.

The descriptions of the optical systems of FIGS. 2 and 4 are meant to be illustrative and not definitive. Persons skilled in the art may be able to provide variations on the basic design of these optical systems in the detecting and measuring a heat pulse in a liquid in a conduit and the subsequent measurement of the flow of the liquid in the conduit.

We claim:

1. A liquid metering system comprising
   a) a conduit along which said liquid flows, a portion of said conduit having a light transmitting wall,
   b) a heater adapted to heat a portion of said liquid at a certain position along said conduit,
   c) a light source adapted to provide illumination of said liquid in said conduit through said light transmitting wall at a position downstream from said heater such that no interference pattern is created by reflections of the illumination by the walls of the conduit, and
   d) an optical sensor positioned to receive only a portion of said illumination reflected from the first transmitting wall liquid interface such that said optical sensor detects a change in the intensity of said reflected illumination due to the change in the index of refraction of said heated portion of said liquid as it moves along the conduit, thereby enabling measurement of the motion of said liquid along said conduit.

2. The system of claim 1 wherein said light transmitting wall of said conduit is transparent.

3. The system of claim 1 wherein the light transmitting wall of said conduit is glass.

4. The system of claim 1 wherein the light transmitting wall of said conduit is a polymer.

5. The system of claim 1 wherein the portion of said conduit with a light transmitting wall has a lumen with a rectangular or square cross section.

6. The system of claim 1 wherein said illumination from said source is visible.

7. A system capable of infusing a pharmaceutical liquid into a patient comprising
   a) a conduit along which said liquid flows, a portion of said conduit having a light transmitting wall,
   b) a heater adapted to heat a portion of said liquid at a certain position along said conduit,
   c) a source providing illumination of said liquid in said conduit through said light transmitting wall at a position downstream from said liquid heater such that no interference pattern is created by reflections of the illumination by the walls of the conduit, and
   d) an optical sensor positioned to receive only a portion of said illumination reflected from the first transmitting wall liquid interface such that said optical sensor detects a change in the intensity of said reflected illumination due to the change in the index of refraction of said heated portion of said liquid as it moves along the conduit, thereby enabling the measurement of flow of the liquid through the conduit.

8. The system of claim 7 wherein said light transmitting wall of said conduit is transparent.

9. The system of claim 7 wherein the light transmitting wall of said conduit is glass.

10. The system of claim 7 wherein the light transmitting wall of said conduit is a polymer.

11. The system of claim 7 wherein the portion of the conduit with a light transmitting wall has a lumen with a rectangular or square cross section.

12. The system of claim 7 wherein said illumination from said light source is visible.

13. The method of measuring liquid flow along a conduit with a light transmitting portion comprising the steps of
   a) healing a portion of the liquid at one location along the conduit,
   b) illuminating a downstream location of the conduit through the light transmitting portion of the conduit with illumination from a light source such that no interference pattern is created by reflections of the illumination by the walls of the conduit,
   c) detecting a change in the intensity of only said illumination reflected from the first transmitting wall liquid interface at the downstream location of the conduit when the heated portion of the liquid passes the downstream location due to the change in the index of refraction of the heated portion of the liquid, and
   d) calculating the time required for the heated portion of the liquid to travel from the location of the heat source to the location of the illumination.

14. The method of claim 13 used in a system to deliver pharmaceutical solutions.

15. The method of measuring liquid flow along a conduit of a) heating a portion of the liquid at one location along the conduit, b) sensing the heated portion of the liquid at a downstream location along the conduit, c) measuring a signal caused by a change in an intensity of only illumination reflected at a first interface of said liquid and said conduit caused by a change in the index of refraction of the heated portion of the liquid as it moves down the conduit wherein said illumination illuminates the conduit such that no interference pattern is created by reflections of the illumination by the walls of the conduit, and d) calculating the time required for the heated portion of the liquid to travel from the heating location to the sensing location.

16. A liquid metering system comprising:
   a conduit along which liquid flows, a portion of the conduit having a wall;
   a liquid heater that heats a portion of the liquid at a first position along the conduit;
   a light source directing a beam of light through the wall for illumination of the liquid in the conduit at a second position downstream of the first position such that no interference pattern is created by reflections of the illumination by the walls of the conduit; and
   an optical detector positioned to detect a change in an the intensity of only the portion of the beam generated by reflection at a first interface between the wall and the liquid;
   wherein the change in the intensity is caused by the change in the index of refraction of the heated portion of the liquid passing the second position.

17. The liquid metering system of claim 16 wherein the optical property is an intensity of the reflected portion of the beam.

18. The liquid metering system of claim 16 wherein the wall is a glass wall or a polymer wall.

19. The liquid metering system of claim 16 wherein the portion of the conduit has a lumen with a rectangular or square cross section.

20. The liquid metering system of claim 16 wherein the beam directed by the light source is visible.

21. The liquid metering system of claim 16 wherein the liquid heater is an infrared laser.

22. A method of metering a liquid comprising the steps of:
   heating a portion of the liquid at a first position along a conduit wherein the conduit has a wall at a second position downstream from the first position;
   directing a beam of light through the wall such that no interference pattern is created by reflections of the illumination by the walls of the conduit; and
   detecting a change in the intensity of only the portion of the beam of light reflected from the first interface of the liquid and the wall at the second position;
   wherein the change in the intensity is caused by the change in the index of refraction of the heated portion of the liquid passing the second position.

23. The method of claim 22 wherein the wall is a glass wall or a polymer wall.

24. The method of claim 22 wherein the conduit has a lumen with a rectangular or square cross section.

25. The method of claim 22 wherein the beam directed is a visible light beam.

26. The method of claim 22 wherein the heating step comprises the step of directing an infrared laser beam to the liquid.

27. The method of claim 22 wherein the optical property is an intensity of the reflected portion of the beam.

* * * * *